United States Patent [19]

Morimoto et al.

[11] Patent Number: 4,476,298

[45] Date of Patent: Oct. 9, 1984

[54] ERYTHROMYCIN A DERIVATIVES

[75] Inventors: Shigeo Morimoto; Yoko Takahashi, both of Saitama; Yoshiaki Watanabe, Tokyo; Sadafumi Omura, Saitama, all of Japan

[73] Assignee: Taisho Pharmaceutical Co., Ltd., Japan

[21] Appl. No.: 444,171

[22] Filed: Nov. 24, 1982

[30] Foreign Application Priority Data

Dec. 3, 1981 [JP] Japan .............................. 56/195039

[51] Int. Cl.$^3$ ............................................ C07H 17/08
[52] U.S. Cl. ..................................................... 536/7.2
[58] Field of Search ......................................... 536/7.2

[56] References Cited

U.S. PATENT DOCUMENTS 2,653,899 9/1953 Bunch et al. .
3,884,904 5/1975 Jones et al. ........................... 536/7.2
4,331,803 5/1982 Watanabe et al. .................... 536/7.2

OTHER PUBLICATIONS

Slawinski et al., *Chemical Abstracts*, vol. 84, 1976, p. 618, Chemical Abstract No. 105987q.
Edwin H. Flynn et al., "Erythromycin. II. Des-N-methylerythromycin and N-Methyl-C$^{14}$-erythromycin".

*Primary Examiner*—Johnnie R. Brown
*Assistant Examiner*—Elli Peselev
*Attorney, Agent, or Firm*—Kenway & Jenney

[57] ABSTRACT

Novel erythromycin A derivatives of the formula

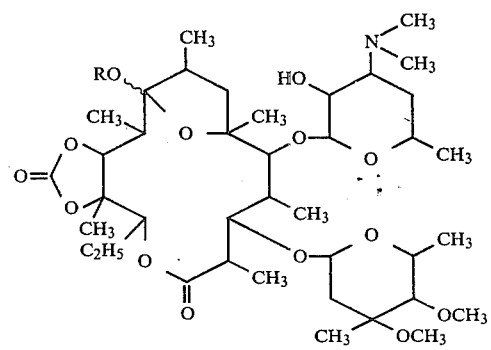

wherein R is hydrogen or methyl, and the pharmaceutically acceptable acid addition salts thereof are disclosed. They exhibit excellent antibacterial activity against erythromycin resistant bacteria, Gram-positive bacteria and Mycoplasma species.

3 Claims, No Drawings

ERYTHROMYCIN A DERIVATIVES

The present invention relates to novel antibacterial agents. More specifically, it is concerned with a novel 11, 12-cyclic carbonate erythromycin A derivatives having strong antibacterial activity against erythromycin resistant bacteria, Gram-positive bacteria and Mycoplasma species.

Some attempts have been made to obtain new compounds effective against erythromycin resistant bacteria. No compound has been found, however, which is effective against both erythromycin resistant bacteria and Gram-positive bacteria.

The present invention is based on the discovery that novel 11, 12-cyclic carbonate erythromycin A derivatives in which one to two of hydroxy groups at the 4''- and 9-positions are substituted by methyl group exhibit strong antibacterial activity against erythromycin resistant bacteria, Gram-positive bacteria and Mycoplasma species.

The compounds of the present invention are erythromycin A derivatives of the formula

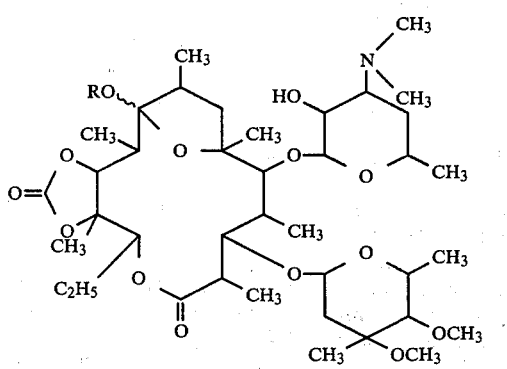

wherein R is hydrogen or methyl, and the pharmaceutically acceptable acid addition salts thereof.

The most preferred compound of the present invention is that of formula I wherein R is hydrogen.

The pharmaceutically acceptable acid addition salts of the compounds of formula I include salts of inorganic acids such as hydrochloric acid, hydrobromic acid, hydroiodic acid, nitric acid, sulfuric acid, sulfurous acid, phosphoric acid and the like, and organic acids such as formic acid, acetic acid, propionic acid, butyric acid, lactic acid, citric acid, malic acid, glycolic acid, tartaric acid, succinic acid, maleic acid, fumaric acid, gluconic acid, stearic acid, mandelic acid, benzoic acid, methanesulfonic acid, aminoethanesulfonic acid, p-toluenesulfonic acid, glutamic acid, aspartic acid and the like.

The compounds of formulae I, II and III presented below exist in two epimeric forms at the 9-position, therefor the formulae in the present specification are generic to and embracive of both of the epimeric forms.

The compound of formula I of the present invention, for example, may be prepared as follows: Namely, 2'-O-benzyloxycarbonyl-N-benzyloxycarbonyl-des-N-methylerythromycin A is added to excess ethylene carbonate in the presence of a base in an inert solvent, and the mixture is allowed to stand at room temperature, or refluxed under heating. The reaction mixture is worked up in a conventional manner to give the 11,12-cyclic carbonate compound of the formula

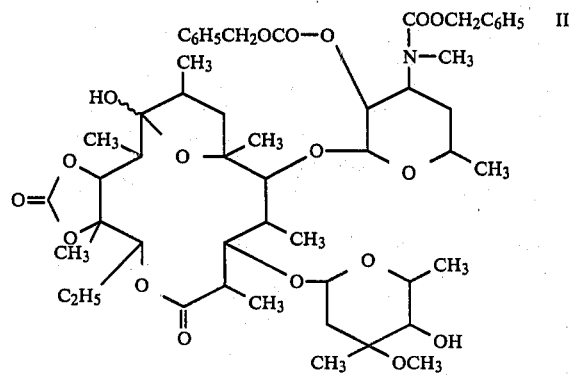

Examples of the inert solvent used are benzene, toluene and the like.

Examples of the base used are sodium carbonate, potassium carbonate and the like.

The compound of formula II may be transferred without isolation to the next reaction, or may be isolated by silica gel column chromatography using a mixture of ethyl acetate and n-hexane(1:2) as a developing solvent.

The compound of formula II thus obtained is reacted with a methylating agent such as methyl iodide, dimethyl sulfate, methyl p-toluenesulfonate or the like, in the presence of a suitable base in a solvent in order to effect methylation of one to two of hydroxy groups at the 4''- and 9-positions of the compound of formula II. The reaction mixture is worked up in a conventional manner to give a compound of the formula

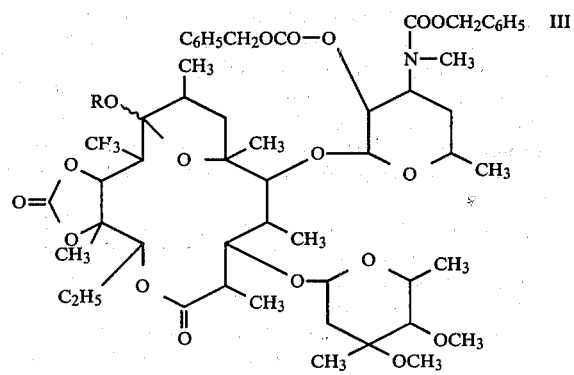

wherein R is as defined above.

Examples of suitable bases are alkali metal hydrides such as lithium hydride, sodium hydride, potassium hydride and the like, alkali metal amides such as lithium amide, sodium amide, potassium amide and the like, butyl lithium, lithium diisopropylamide and the like.

In the reaction to obtain the compound of formula III from the compound of formula II, 5–10 moles of the methylating agent and 1–3 moles of the base are employed per mole of the compound of formula II, and they are allowed to react at −78° C. to room temperature, preferrably at −5° to 5° C.

The solvents which may be used include inert solvents in which the compound of formula II is dissolved, for example, polar aprotic solvents such as N,N-dimethylformamide, N,N-dimethylacetamide and the like.

The compound of formula III thus obtained may be transferred without isolation to the next reaction, or may be isolated by silica gel column chromatography.

The compound of formula III is catalytically reduced according to the method reported by E. H. Flynn et al. in Journal of the American Chemical Society, 77, page 3104(1955) in order to eliminate benzyloxycarbonyl group, and then subjected to further catalytic reduction in the presence of excess formaldehyde to effect N-methylation.

The intermediate thus obtained by catalytic reduction for elimination of benzyloxycarbonyl group may be used without isolation, or after isolation in a conventional manner, for N-methylation.

The crude product thus obtained may be processed by silica gel column chromatography (Art. 7734 produced by E. Merck Darmstadt, and a mixture of chloroform and methanol(100:2–100:5) as a developing solvent) to give fractions. Thin layer silica gel chromatography (using Art. 13727 produced by E. Merck Darmstadt, and a mixture of chloroform and methanol (4:1) as a developing agent) was used in the detection of the product for each fraction, and there are obtained fractions having a spot at Rf of 0.47(hereinafter referred to as Fraction A), fractions having a spot at Rf of 0.44 (hereinafter referred to as Fraction B) and fractions having a spot at Rf of 0.40 (hereinafter referred to as Fraction C).

After treatment of each fraction in a conventional manner, there are obtained a single epimer of the compound of formula I wherein R is methyl group from Fraction A, the other epimer of the compound of formula I wherein R is methyl from Fraction B, and a single epimer of the compound of formula I wherein R is hydrogen atom from Fraction C.

A pharmaceutically acceptable acid addition salt of the compound of formula I may be obtained by treating the compound of formula I with one mole equivalent of the corresponding acid described above in an inert solvent such as water, acetone, methanol or ethanol. The salts thus obtained are collected by filtration if they are insoluble in the inert solvent, by precipitation by addition of a non-solvent for the salt, or by evaporation of the solvent.

2'-O-benzyloxycarbonyl-N-benzyloxycarbonyl-des-N-methylerythromycin A used as a starting material can be prepared according to the above-described method of E. H. Flynn et al.

The compounds of the present invention are not only effective against those bacteria against which erythromycin is effective but are also especially effective against erythromycin resistant bacteria and, therefore, they are useful as antibacterial agents. For use as a antibiotic, a compound of formula I may be administered orally or parenterally in a conventional dosage form such as tablet, capsule, powder, troche, dry mix, ointment, suspension or solution prepared according to conventional pharmaceutical practices.

The compounds of the present invention can be administered at a dosage of from about 1 mg/kg to about 100 mg/kg of body wight per day. The preferred dosage range is from about 2 mg/kg to about 25 mg/kg of body weight per day.

The compounds of the present invention have excellent low toxicity. The $LD_{50}$ value in mice is in excess of 5000 mg/kg of body weight.

The present invention is further illustrated by the following examples.

Example 1

(1) To 300 ml of dry benzene were added 50 g of 2'-O-benzyloxycarbonyl-N-benzyloxycarbonyl-des-N-methylerythromycin A, 25 g of potassium carbonate and 50 g of ethylene carbonate. The mixture was refluxed for 2 hours under heating. To the cooled mixture was added water, and the benzene layer was separated, washed with a saturated aqueous sodium chloride solution and dried over anhydrous magnesium sulfate. Evaporation of the benzene in vacuo gave the residue, which was then fractionated by silica gel chromatography (silica gel 60 for column chromatography produced by E. Merck Darmstadt, 70–230 mesh, $\phi$ 5.5 cm ×40 cm; and a mixture of ethyl acetate and n-hexane(1:2) as a developing solvent), and 300 ml of each of the fractions were collected. Thin layer chromatography (precoated thin layer chromatography plate silica gel 60 $F_{254}$ produced by E. Merck Darmstadt; and a mixture of ethyl acetate and n-hexane(1:1) as a developing solvent) was applied to the detection of the product of each fraction, and the fractions 7–12 having a spot at Rf value of 0.59 were collected. After evaporation of the solvent, recrystallization from ether gave 24.27 g of a single epimer of the compound of formula II as colorless crystals.

m.p. 197.5°–199.0° C. (with decomposition)

Elemental analysis (for $C_{53}H_{75}NO_{18}$): Calcd. (.%): C, 62.77; H, 7.45; N, 1.38. Found. (%): C, 62.80; H, 7.55; N, 1.33.

FD-Mass (m/e): 1013 (M+).

IR $\nu_{max}^{KBr}$ cm$^{-1}$: 3520, 1800, 1755, 1700

$^1$H-NMR(CDCl$_3$): $\delta$=2.81, 2.84(3H), 5.00–5.20 (m, 4H), 7.25–7.42(m, 10H).

(2) In 100 ml of dry N,N-dimethylformamide were dissolved 19 g of the compound of formula II obtained in item(1) and 12 ml of methyl iodide. The solution was stirred under cooling at 0° C.–5° C. in a nitrogen stream, and 1.7 g of a 60% sodium hydride dispersion was added thereto in small increments with stirring. Stirring was continued for a further 2.5 hours.

After completion of the reaction, 40 ml of triethylamine was added with stirring under ice-cooling, 200 ml of a saturated aqueous sodium chloride solution was added, and the mixture was extracted with ethyl acetate. The ethyl actate layer was collected, washed with a saturated aqueous sodium chloride solution, and dried over anhydrous magnesium sulfate, and evaporation of the solvent gave the crude product.

The crude product thus obtained was fractionated by silica gel chromatography (silica gel Art. 7734 produced by E. Merck Darmstadt, and a mixture of n-hexane and ethyl acetate(2:1) as a developing solvent). Thin layer chromatography (silica gel Art. 5715 produced by product of E. Merck Darmstadt, and a mixture of n-hexane and ethyl acetate (1:1) as a developing solvent) was applied to the detection of the product for each fraction, the fractions having a spot at Rf value of 0.44 were collected (cf., Rf value of the starting material, 0.41), and the solvent was evaporated in vacuo, affording 11.8 g of a colorless foam.

(3) 11 g of the foam obtained in (2) was dissolved in a mixture of 1.4 g of sodium acetate, 0.88 ml of acetic acid, 40 ml of water and 200 ml of ethanol, to which 1.0 g of palladium black was added. The mixture was stirred for 5 hours at ambient temperature under atmospheric pressure in a gentle hydrogen stream in order to effect catalytic reduction. Next, into this was poured 25 ml of a 37% aqueous formaldehyde solution, and catalytic reduction was continued for a further 4 hours. After completion of the reaction, the catalyst was filtered off, and the solvent was distilled off. To the residue was added 100 ml of water, and the mixture was adjusted to about pH 10 with a saturated aqueous sodium carbonate solution. This was extracted with methylene chloride, and the methylene chloride layer was collected, washed with a saturated aqueous sodium chloride solution, and dried. After evaporation of the solvent, the crude product thus obtained was fractionated by silica gel column chromatography (silica gel Art. 7734 produced by E. Merck Darmstadt, $\phi$ 4.4×40 cm, and a mixture of chloroform and methanol (100:2)–(100:5) as a developing solvent), and 15 ml of each of the fractions were collected. Thin layer chromatography (silica gel Art. 13727 produced by E. Merck Darmstadt: and a mixture of chloroform and methanol (4:1) as a developing solvent) was applied to the detection of the product for each fraction, and there were collected the fractions 43–58 of Fraction A having a spot at Rf value of 0.47, the fractions 66–100 of Fraction B having a spot at Rf value of 0.44, and the fractions 120–210 of Fraction C having a spot at Rf value of 0.40 (cf., Rf value of the starting material, 0.32).

Evaporation of the solvent of Fractin A gave 0.86 g of a single epimer of the compound of formula I wherein R is methyl.

m.p. 121°–124.5° C. (with decomposition)

Mass (m/e): 787 (M $^{30}$)

IR $\nu_{max}^{KBr}$ cm$^{-1}$: 1810, 1735

$^1$H-NMR(CDCl$_3$) : $\delta$=2.29(s, 6H), 3.29(s, 3H), 3.31(s, 3H), 3.56(s, 3H).

Similarly, 1.3 g of the other epimer of the compound described above was obtained from Fraction B.

m.p. 120.5°–123.5° C. (with decomposition)

Mass (m/e): 787 (M$^+$)

IR $\nu_{max}^{KBr}$cm$^{-1}$ : 1810,1735

$^1$H-NMR(CDCl$_3$) : $\delta$=2.03(s, 6H), 3.22(s, 3H), 3.30(s, 3H), 3.56(s, 3H)

Similarly, 4.8 g of a single epimer of the compound of formula I wherein R is hydrogen atom was obtained from Fraction C.

m.p. 122°–126° C. (with decomposition)

Mass (m/e): 773 (M$^{30}$)

IR $\nu_{max}^{KBr}$cm$^{-1}$: 3400–3520, 1805, 1735

$^1$H-NMR(CDCl$_3$): $\delta$=2.28(s, 6H), 3.34(s, 3H), 3.57(s, 3H).

EXAMPLE 2

(1) Following the method of Example 1(2) and using 20 g of the compound of formula II, 12.6 g of dimethyl sulfate, 120 ml of dry N,N-dimethylformamide and 2 g of 60% sodium hydride dispersion, there was obtained 12.6 g of a colourless foam.

(2) Following the method of Example 1(3) and using 12 g of the foam, there were obtained 3.5 g of a single epimer of the compound of formula I wherein R is methyl 0.8 g of the other epimer of the compound described above, and 1.6 g of a single epimer of the compound of formula I wherein R is hydrogen.

The properties of these compounds where identical with those of the compounds obtained from Fractions A, B and C in Example 1.

The following experiment illustrates antibacterial spectrum of the compounds of the present invention.

Experiment 1

Erythromycin A was used as a control, and the compounds of formula I derived from Fractions A, B and C were tested for antibacterial activity against various bacteria by the agar plate dilution method. The results, indicated as the MIC value (minimal inhibitory concentrations, mcg/ml), are shown in the following table.

| Microorganism | Antibacterial spectrum MIC value (mcg/ml) | | | |
|---|---|---|---|---|
| | | Test Compound | | |
| | | | Compound I | |
| | control | A | B | C |
| *Staphylococcus aureus* FDA 209 P | ≦0.05 | ≦0.05 | 0.1 | ≦0.05 |
| *Staphylococcus aureus* smith | 0.2 | 0.4 | 0.8 | 0.2 |
| *Staphylococcus epidermidis* IID 866 | 0.4 | 0.4 | 0.8 | 0.4 |
| *Streptococcus faecalis* ATCC 8043 | ≦0.05 | ≦0.05 | 0.1 | ≦0.05 |
| *Micrococcus luteus* NIHJ | <0.05 | <0.05 | <0.05 | <0.05 |
| *Staphylococcus aureus* TPR 13* | 25 | 1.6 | 3.1 | 0.8 |
| *Staphylococcus aureus* TPR 23* | 100 | 3.1 | 6.25 | 3.1 |
| *Staphylococcus aureus* TPR 25* | 50 | 1.6 | 3.1 | 0.8 |
| *Bacillus subtilis* EM-R* | >100 | 0.4 | 0.8 | 0.4 |

(Note)
*Strain resistant to erythromycin
A: the compound derived from Fraction A
B: the compound derived from Fraction B
C: the compound derived from Fraction C

What is claimed is:

1. An erythromycin A derivative of the formula

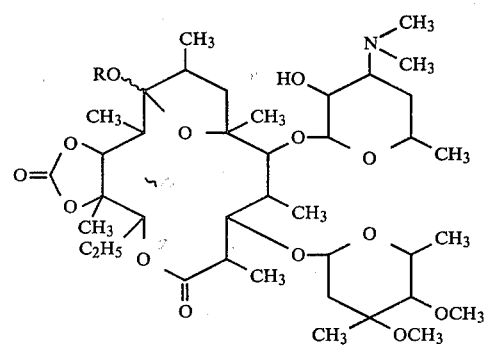

wherein R is hydrogen or methyl, and the pharmaceutically acceptable acid addition salts thereof.

2. A compound according to claim 1 wherein R is hydrogen.

3. A compound according to claim 1 wherein R is methyl.

UNITED STATES PATENT AND TRADEMARK OFFICE
CERTIFICATE OF CORRECTION

PATENT NO. : 4,476,298

DATED : Oct. 9, 1984

INVENTOR(S) : Shigeo Morimoto, Yoko Takahashi, Yoshiaki Watanabe and Sadafumi Omura, all of Japan It is certified that error appears in the above-identified patent and that said Letters Patent is hereby corrected as shown below:

Col. 5, line 28 "Fractin" should read --Fraction--;

Col. 5, line 32 "$M^{30}$" should read --$M^+$--;

Col. 5, line 42 "2.03" should read --2.30--;

Col. 5, line 48 "$M^{30}$" should read --$M^+$--;

Col. 5, line 63, after "methyl" insert a comma --,--.

Signed and Sealed this

Sixteenth Day of April 1985

[SEAL]

Attest:

DONALD J. QUIGG

Attesting Officer     Acting Commissioner of Patents and Trademarks